(12) United States Patent
Shanker et al.

(10) Patent No.: US 10,336,685 B2
(45) Date of Patent: Jul. 2, 2019

(54) CRYSTALLINE MODIFICATION OF PROPANIL

(71) Applicant: UPL LIMITED, Mumbai (IN)

(72) Inventors: Birja Shanker, Mumbai (IN); Jaidev Rajnikant Shroff, Mumbai (IN); Vikram Rajnikant Shroff, Mumbai (IN)

(73) Assignee: UPL LIMITED, Mumbai (IN)

( * ) Notice: Subject to any disclaimer, the term of this patent is extended or adjusted under 35 U.S.C. 154(b) by 0 days.

(21) Appl. No.: 15/544,717

(22) PCT Filed: Dec. 31, 2015

(86) PCT No.: PCT/IB2015/060072
§ 371 (c)(1),
(2) Date: Jul. 19, 2017

(87) PCT Pub. No.: WO2016/116797
PCT Pub. Date: Jul. 28, 2016

(65) Prior Publication Data
US 2017/0369423 A1    Dec. 28, 2017

(30) Foreign Application Priority Data

Jan. 19, 2015 (IN) .............................. 67/KOL/2015

(51) Int. Cl.
| | | |
|---|---|---|
| *A01N 37/22* | (2006.01) | |
| *A01N 37/10* | (2006.01) | |
| *A01N 43/40* | (2006.01) | |
| *A01N 43/54* | (2006.01) | |
| *A01N 43/80* | (2006.01) | |
| *A01N 39/04* | (2006.01) | |
| *A01N 47/36* | (2006.01) | |
| *C07C 233/15* | (2006.01) | |
| *C07C 231/24* | (2006.01) | |

(52) U.S. Cl.
CPC ............ *C07C 233/15* (2013.01); *A01N 37/10* (2013.01); *A01N 37/22* (2013.01); *A01N 39/04* (2013.01); *A01N 43/40* (2013.01); *A01N 43/54* (2013.01); *A01N 43/80* (2013.01); *A01N 47/36* (2013.01); *C07C 231/24* (2013.01); *C07B 2200/13* (2013.01)

(58) Field of Classification Search
None
See application file for complete search history.

(56) References Cited

U.S. PATENT DOCUMENTS 3,158,650 A    11/1964    Weil et al.
3,816,092 A    6/1974    Wilson et al.

FOREIGN PATENT DOCUMENTS

GB    1063528    3/1967

OTHER PUBLICATIONS

The International Search Report issued in International application No. PCT/IB2015/060072, dated Mar. 18, 2016.

*Primary Examiner* — Alton N Pryor
(74) *Attorney, Agent, or Firm* — IP Pundit LLC (57) ABSTRACT

The present invention relates to crystalline modification of (3,4-dichlorophenyl)propanamide (propanil), to a process for the preparation of the same, to pesticidal mixtures and compositions comprising the crystalline modification of 5 (3,4-di-chlorophenyl)propanamide and to a method of combating weeds using said mixtures and compositions.

12 Claims, 6 Drawing Sheets

CRYSTALLINE MODIFICATION OF PROPANIL

CROSS REFERENCE TO RELATED APPLICATIONS

This application is a national phage application under 35 U.S.C. § 371 of International Application No. PCT/IB2015/060072, filed on Dec. 31, 2015, which claims priority to Indian Patent Application No. 67/KOL/2015, filed on Jan. 19, 2015, the disclosures of all of which are incorporated herein by reference in their entirety.

TECHNICAL FIELD OF THE INVENTION

The present invention relates to crystalline modification of N-(3,4-dichlorophenyl) propanamide, to a process for the preparation of the same, to pesticidal combinations and compositions comprising said crystalline modification and to a method of controlling weeds using the same.

BACKGROUND OF THE INVENTION

N-(3,4-dichlorophenyl)propanamide is a herbicide which is known under a common name of propanil. Various processes for the preparation of propanil have been described. For example, GB903766, U.S. Pat. No. 3,382,280, GB1063528, CN1775745 and U.S. Pat. No. 3,158,650 disclose detailed preparation procedures for propanil.

GB903766 relates to preparation of propanil. Recrystallization of the final product has been carried out using aqueous methanol. GB903766 discloses the melting point of propanil as 91° C.

U.S. Pat. No. 3,382,280 discloses the preparation as well as recrystallization of propanil using cyclohexane.

However, none of the prior art mention about different crystalline forms having different physical forms and properties.

Characterization of propanil obtained by the processes described in the prior art is usually done by the analytical method such as NMR and melting point determination. In the Pesticidal Manual 13$^{th}$ Edition, propanil is described as colorless odourless crystals with a melting point of 91.5° C. The described melting points in the prior art is in the range of 91°-93° C.

Properties of different crystalline forms of a compound vary from one form to another in many ways. Examples of such properties specific to certain forms of a compound are colour, solubility, crystal size and shape, particle density, flowability, melting point, thermal stability and reactivity. For the large-scale manufacture and formulation of a commercial product such as propanil which is available as flakes, it is of crucial importance to know whether different crystalline modification of compounds exist or how can they be prepared and characterized. Such crystalline forms are of high relevance as they may lead to better bioefficacy and consequently a reduction in dosage of the pesticide which again has a direct impact on environment in a positive manner.

Propanil is a widely used contact herbicide. It is one of the more widely used herbicide in rice fields. It has been used at a dosage of upto 5.0 kg/ha to control many broad-leaved and grass weeds, including *Amaranthus retroflexus*, *Digitaria* spp., *Echinochloa* spp., *Panicum* spp., and *Setaria* spp. It has been noted that large quantities of propanil is required for the effective control of the weeds which raise health and environmental concerns in using propanil.

Considering the wide scale use of propanil for effective post-emergent control of many broad-leaf weeds, a reduction in usage could be a better choice to have a direct impact on associated hazardous and toxicological problems on prolonged usage which in turn will help to continue the use of this herbicide effectively.

It has now been found out that propanil exists in a different crystal form having very advantageous properties such as better bioefficacy.

Disclosure on different crystalline modification of propanil as well as preparation procedure and characterization of any such crystalline modification of propanil is hitherto unknown.

OBJECTS OF THE INVENTION

Accordingly, it is an object of the present invention to provide a crystalline modification of propanil.

It is another object of the present invention to provide a process for the preparation of the crystalline modification of propanil.

Another object of the present invention is to prepare the crystalline modification of propanil in high yield and purity.

Yet another object of the present invention is to provide an economically viable process for the preparation of the crystalline modification of propanil.

It is an object of the present invention to provide agrochemical combinations comprising the crystalline modification of propanil.

Yet another object of the present invention is to provide agrochemical compositions comprising the crystalline modification of propanil.

It is another object of the present invention to provide a process for preparing agrochemical compositions comprising the crystalline modification of propanil.

It is another object of the present invention to provide a method of controlling weeds comprising agrochemical compositions comprising the crystalline modification of propanil.

SUMMARY OF THE INVENTION

The present invention provides a crystalline modification of propanil.

Further it relates to a process for preparation of a crystalline modification of propanil.

The present invention further relates to agrochemical compositions comprising a crystalline modification of propanil.

The present invention also provides process for preparing compositions comprising a crystalline modification of propanil.

There is also provided agrochemical combinations comprising a crystalline modification of propanil with one or more other pesticides.

Further there is provided agrochemical compositions comprising a crystalline modification of propanil in combination with one or more other pesticides and a process for preparing such compositions.

In another aspect there is provided a method of using a crystalline modification of propanil for effectively controlling undesired weed species.

DETAILED DESCRIPTION OF THE INVENTION

The inventors of the present invention surprisingly found out that propanil exist in different crystalline forms. Accordingly there is provided a crystalline modification of propanil and a process for preparation of the crystalline modification.

Surprisingly it has been observed that the crystal morphology of propanil (technical sample) changes intensely with variation in the polarity of the solvent in which crystallisation is carried out.

Accordingly, there is provided crystalline propanil.

Further there is provided a process for the preparation of the crystalline proapnil.

Most surprisingly, it has been observed that the crystalline propanil leads to enhanced bioefficacy.

Accordingly there is provided agrochemical compositions comprising the crystalline propanil.

Inventors of the present invention also observed that agrochemical combinations comprising crystal modification of propanil resulted in better bioefficacy in controlling the undesired weed species.

Accordingly, there is provided agrochemical combinations comprising crystalline propanil with one or more other pesticides.

Further there is provided a process for preparation of agrochemical compositions comprising crystalline modification of propanil.

Accordingly there is provided agrochemical compositions comprising crystalline modification of propanil in combination with one or more other pesticides.

Further there is provided a process for preparation of agrochemical compositions comprising crystalline modification of propanil in combination with one or more pesticides.

As used herein, the phrase crystalline modification of propanil shall be understood to mean the crystalline propanil according to the present invention.

In an aspect, the present invention provides a process for the preparation of crystalline propanil, said process comprising crystallizing propanil from a halogenated hydrocarbon solvent.

In an embodiment, the process comprises crystallizing propanil from a solvent mixture comprising at least one halogenated hydrocarbon solvent and at least a second organic solvent.

In an embodiment, the precise chemical procedure which may be used to crystallize propanil is not particularly limiting and may be carried out by a skilled technician as per the standard conventional procedure as long as the criticality of the selected solvent is maintained.

In another embodiment, the crystalline modification of propanil according to the present invention was prepared by a process comprising the following steps:
 a) preparing a concentrated solution of propanil in a halogenated hydrocarbon solvent or in a mixture of a halogenated hydrocarbon solvent and one or more organic solvents;
 b) cooling the solution; and
 c) effecting the crystallisation.

In an embodiment of the present invention, the halogenated hydrocarbon solvent is selected from halogenated lower hydrocarbons from $C_1$ up to $C_6$ carbon atoms.

According to another embodiment the halogenated hydrocarbon solvent is selected from the group consisting of dichloromethane, dichloropropane, trichloroethane, chloroform and dichloroethane.

In a preferred embodiment of the present invention, the halogenated hydrocarbon solvent is selected from dichloromethane or dichloroethane.

In an embodiment of the present invention, the solvent is a mixture of halogenated hydrocarbon solvent and one or more organic solvents.

In an embodiment of the present invention, the organic solvent is a non-polar organic solvent.

In another embodiment of the present invention, the non-polar organic solvent is selected from but not limited to aliphatic or aromatic hydrocarbon solvents or ether solvents.

In a preferred embodiment of the present invention, the non-polar organic solvent is selected from but not limited to pentane, cyclopentane, hexane, cyclohexane, heptane, octane, benzene, toluene, 1,4-dioxane, or diethyl ether.

In an embodiment of the present invention, the temperature at which the concentrated solution of propanil may be prepared is varied from about 30°- to about 120° C.

In an embodiment of the present invention, during step (b), concentrated solution of technical propanil is cooled to a temperature which varies from about 0°- to about 25° C.

According to a preferred embodiment of the present invention, the crystallisation is effected at a temperature which varies from about 0°- to about 15° C.

The term effecting in step (c) refers to stirring the solution to initiate crystallisation.

According to another preferred embodiment of the present invention, the crystals are isolated at a temperature which varies from about 0°- to about 15° C.

According to a preferred embodiment of the present invention, crystalline propanil propanil was prepared by a process comprising the following steps:
 a) preparing a solution of propanil in halogenated hydrocarbon solvent at a temperature range from about 30°- to about 120° C.;
 b) cooling the mixture to a temperature range of about 0°- to about 25° C.; and
 c) effecting the crystallisation at a temperature range of from about 0°- to about 15° C.

According to another preferred embodiment of the present invention, crystalline propanil was prepared by a process comprising the following steps:
 a) preparing a solution of propanil in a mixture of halogenated hydrocarbon solvent and at least one non-polar solvent at a temperature range of from about 30°- to about 120° C.;
 b) cooling the mixture to a temperature range of about 0°- to about 25° C.; and
 c) effecting the crystallisation at a temperature range of about 0°- to about 15° C.

In an embodiment, the prepared crystals are isolated by filtration.

In an aspect, the present invention provides crystalline propanil.

In a preferred embodiment the present invention provides crystalline propanil prepared by a process comprising the following steps:
 a) preparing a concentrated solution of propanil in a halogenated hydrocarbon solvent or in a mixture of a halogenated hydrocarbon solvent and one or more organic solvents;
 b) cooling the solution; and
 c) effecting the crystallisation.

The crystalline propanil according to the present invention possesses a characteristic X-ray powder diffraction pattern, which is alternately be expressed in terms of the 2-θ and d-spacings parameters.

In an embodiment there is provided crystalline modification of propanil which exhibits an X-ray diffraction pattern having characteristic peaks expressed in 2θ (±0.2°) at at least three of the following positions: 12.51, 14.93, 17.11, 19.8, 21.35, 21.83, 22.91, 23.55, 24.91, 26.09, 29.27, 32.13, 31.07, 38.13 and 39.91.

In another embodiment there is provided crystalline modification of propanil which exhibits an X-ray diffraction pattern having characteristic peaks expressed in 2θ (±0.2°) at 12.51, 14.93, 17.11, 19.8, 21.35, 21.83, 22.91, 23.55, 24.91, 26.09, 29.27, 32.13, 31.07, 38.13 and 39.91.

In another embodiment, the present invention provides crystalline modification propanil characterized by the following X-ray powder diffraction pattern expressed in terms of the 2-θ and d-spacings:

TABLE 1

| d(Å) | 2θ |
| --- | --- |
| 7.064 ± 0.1° | 12.51 ± 0.2° |
| 5.92 ± 0.1° | 14.93 ± 0.2° |
| 5.168 ± 0.1° | 17.11 ± 0.2° |
| 4.464 ± 0.1° | 19.87 ± 0.2° |
| 4.155 ± 0.1° | 21.35 ± 0.2° |
| 4.065 ± 0.1° | 21.83 ± 0.2° |
| 3.875 ± 0.1° | 22.91 ± 0.2° |
| 3.771 ± 0.1° | 23.55 ± 0.2° |
| 3.57 ± 0.1° | 24.91 ± 0.2° |
| 3.41 ± 0.1° | 26.09 ± 0.2° |
| 3.047 ± 0.1° | 29.27 ± 0.2° |
| 2.782 ± 0.1° | 32.13 ± 0.2° |
| 2.8742 ± 0.1° | 31.07 ± 0.2° |
| 2.363 ± 0.1° | 38.13 ± 0.2° |
| 2.258 ± 0.1° | 39.91 ± 0.2° |

The crystalline modification of propanil according to the present invention possesses characteristic structural coordinates.

Therefore, in another embodiment, the present invention provides crystalline modification of propanil having the structure defined by the following structural coordinates:

TABLE 2

| Parameter | Value |
| --- | --- |
| Crystal system | Monoclinic |
| Space group | P2$_1$/c |
| a | 17.8853(2) Å |
| b | 11.6179(1) Å |
| c | 9.8524(9) Å |
| α | 90.00° |
| β | 92.761(6)° |
| γ | 90.00° |
| Volume | 2044.8(3) Å$^3$ |
| Z | 4 |
| Density (calculated) | 1.417 g/cc |

Further, propanil was recrystallized from aqueous methanol (hereinafter referred to as prior art 1 or PA1) as per the literature and compared with the crystalline modification as per the present invention.

Figure 3:
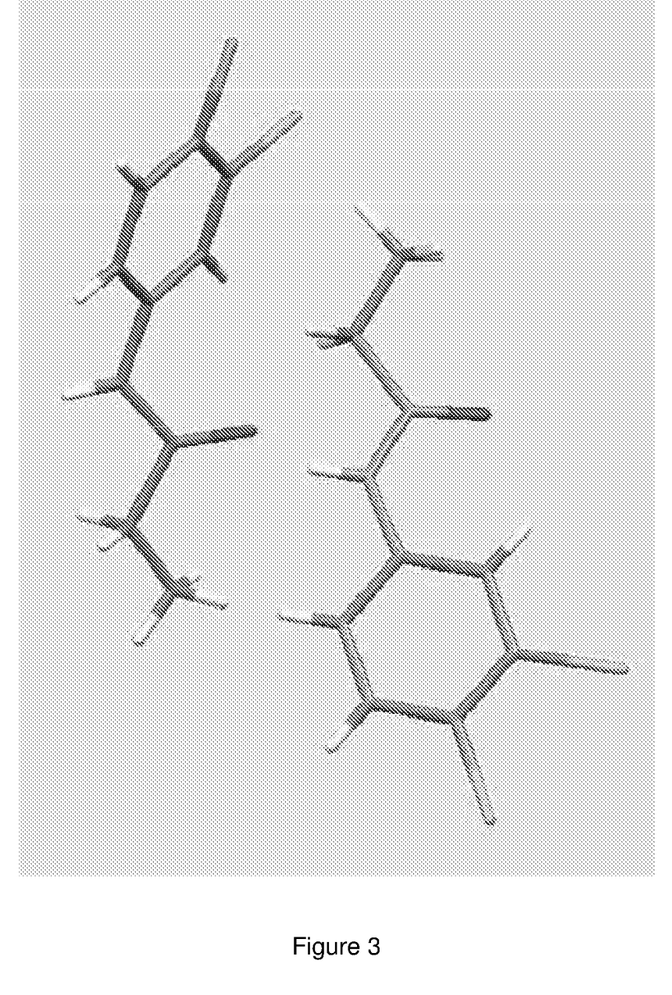
FIG. 3 illustrates single crystal X-ray diffraction studies showing two molecules in the asymmetric unit in crystalline modification of the present invention and the molecules are oriented in opposite direction.

In this aspect, the present invention provides crystalline modification of propanil having a spatial orientation of molecules within the crystals defined by the FIG. 3.

In another aspect, the present invention provides a crystal of propanil, said crystal comprising two molecules in its asymmetric unit, said molecules being oriented in opposite directions.

In an embodiment, the present invention provides crystalline propanil, said crystalline propanil comprising crystals of propanil comprising two molecules in its asymmetric unit, said molecules being oriented in opposite directions.

Figure 4:
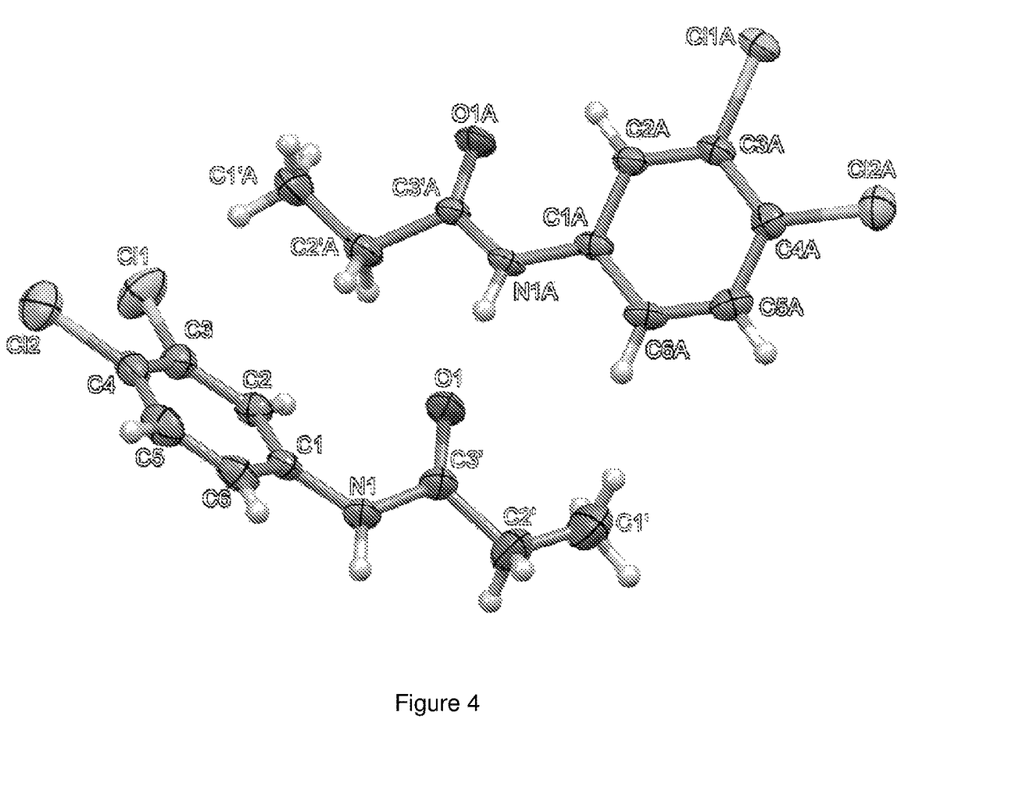
FIG. 4 illustrates crystalline propanil comprising crystals of propanil comprising two molecules in its asymmetric unit, said two molecules being conformationally oriented at an angle of about 65.2° relative to each other about the C1-N1 bond.

In an embodiment, the present invention provides crystalline propanil, said crystalline propanil comprising crystals of propanil comprising two molecules in its asymmetric unit, said molecules being oriented in opposite directions having a spatial arrangement of atoms in one molecule disposed relative to the atoms in the second molecule defined by the following ORTEP depicted in FIG. 4.

In an embodiment, the present invention provides crystalline propanil, said crystalline propanil comprising crystals of propanil comprising two molecules in its asymmetric unit, said two molecules being conformationally oriented at an angle of about 65.2° relative to each other about the C1-N1 bond.

Without wishing to be bound by theory, it is believed that the relative orientation about the C1-N1 bond between the two molecules in the asymmetric unit of the crystalline propanil of the present invention occurs due to the free conformational rotation about the C1-N1 bond.

Figure 6:
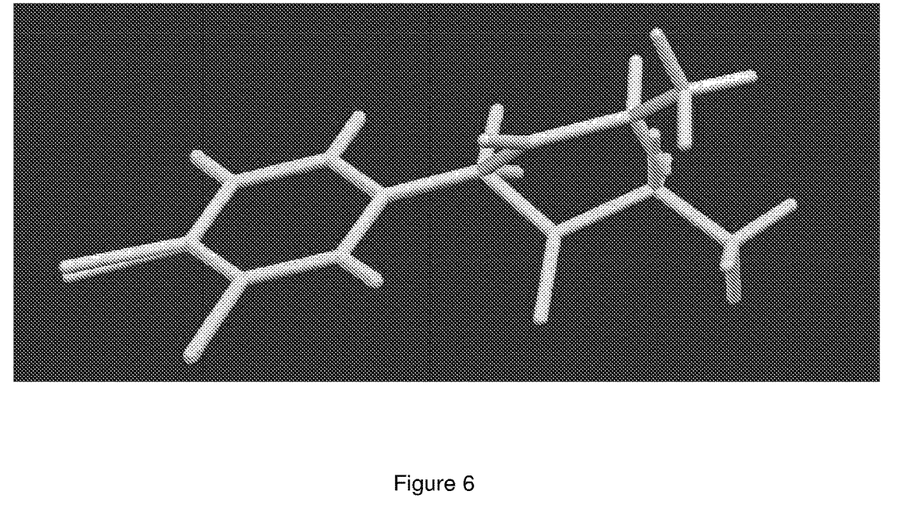
FIG. 6 illustrates overlap of the second molecule of the crystalline propanil of the present invention via-a-vis the crystalline propanil conventionally known displayed different orientation of the side chain.

The spatial arrangement of atoms in the second molecule in the crystalline propanil according to the present invention was compared with the spatial arrangement of atoms in the crystalline propanil conventionally known and described in FIG. 6.

Thus, it was concluded that the crystalline propanil of the present invention differed from the crystalline propanil conventionally known in the spatial orientation of the two molecules in the crystals relative to each other. Surprisingly, it was found that this different spatial orientation of the two molecules relative to each other was the origin of significant enhancement in the herbicidal efficacy of propanil crystals according to the present invention.

Figure 1:
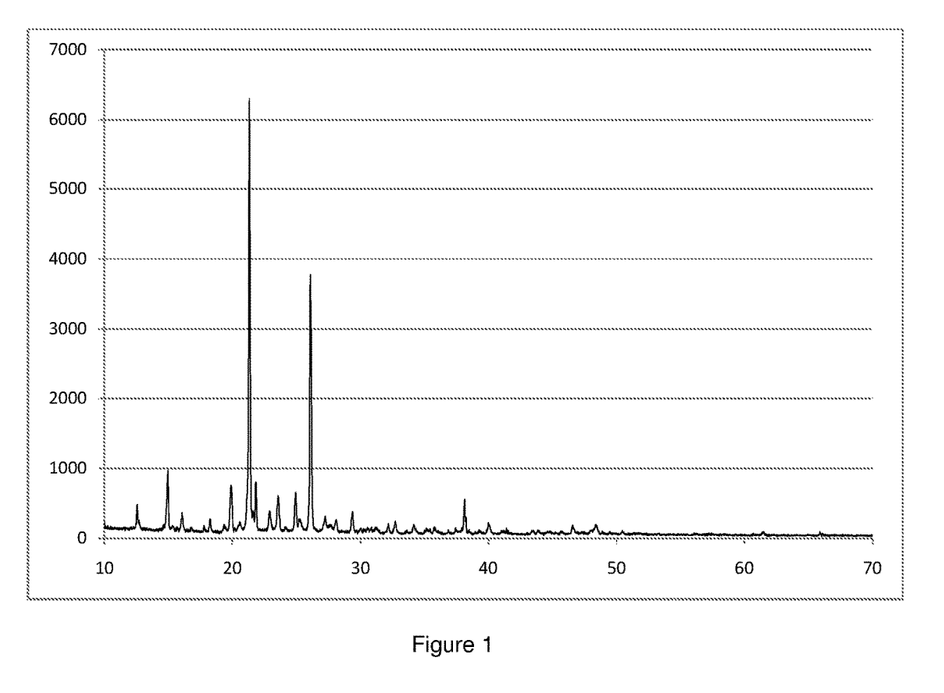
FIG. 1 illustrates X-ray powder diffraction pattern of crystalline modification of propanil.
Figure 2:
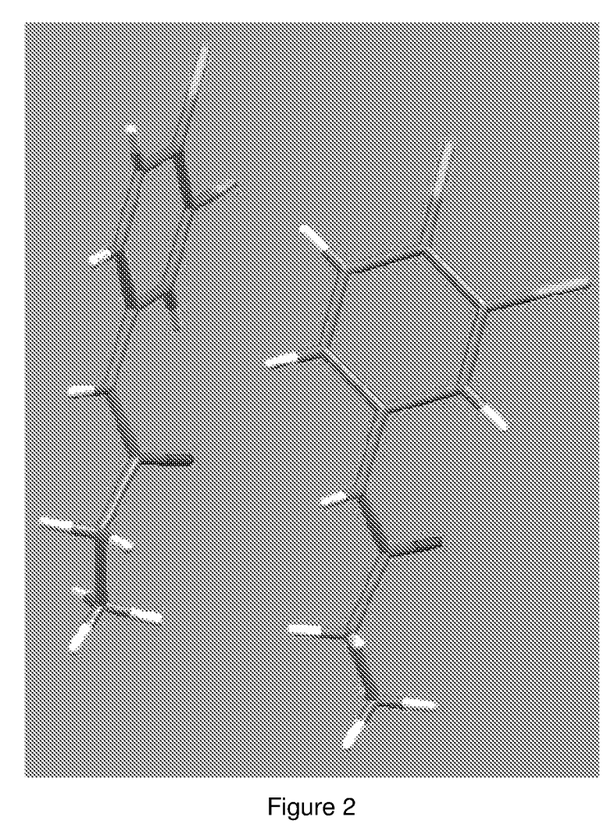
FIG. 2 illustrates single crystal X-ray diffraction studies showing two molecules in the asymmetric unit in PA1 i.e. in known crystal form and both molecules have the side chains on the same side.
Figure 5A:
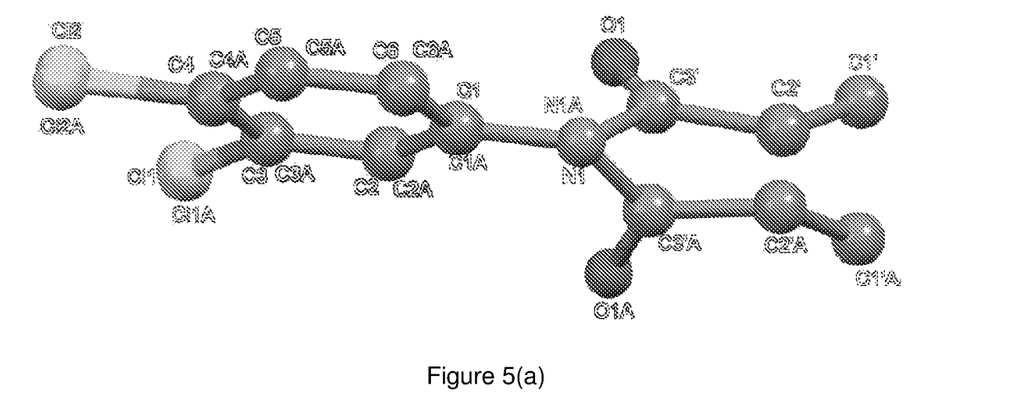
FIG. 5a illustrates crystalline propanil comprising crystals of propanil comprising two molecules in its asymmetric unit, said two molecules being conformationally oriented at an angle of about 65.2° relative to each other about the C1-N1 bond.
Figure 5B:
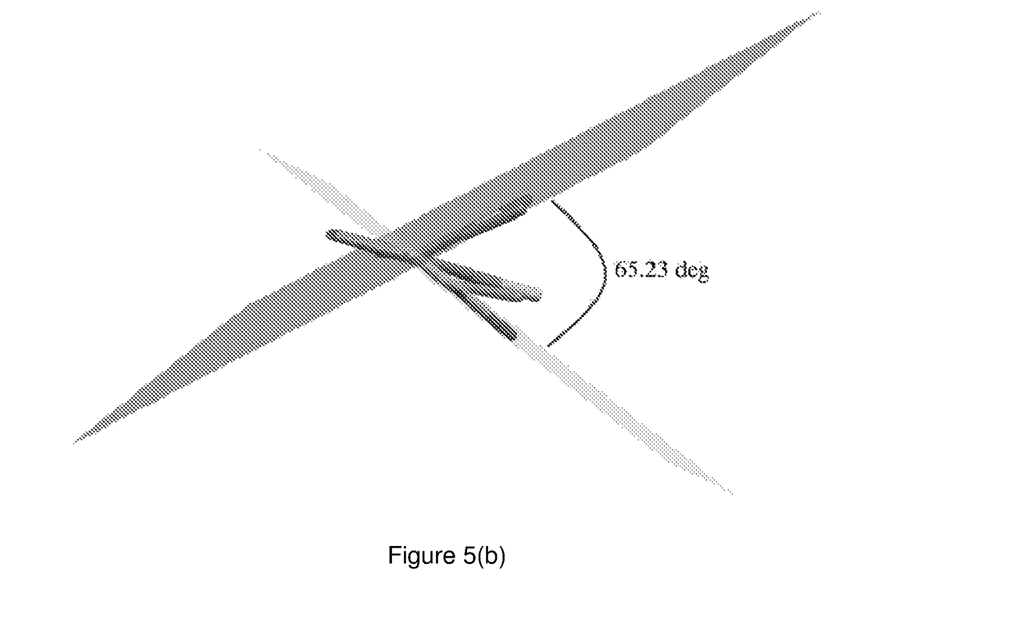
FIG. 5b illustrates crystalline propanil comprising crystals of propanil comprising two molecules in its asymmetric unit, said two molecules being conformationally oriented at an angle of about 65.2° relative to each other about the C1-N1 bond.

In this context, the term crystalline modification of propanil according to the present invention defines, and include, the crystalline modification of propanil having the characteristic spatial orientation of the molecules within the crystal as defined in any aspect or embodiment described hereinabove, particularly with reference to:

(a) the X-ray powder diffraction pattern described in FIG. 1; or
(b) the 2-θ and d-spacings parameters described in table 1; or
(c) the structural coordinates described in table 2; or
(d) the spatial orientation of molecules within the crystals defined by the FIG. 3; or
(e) the spatial arrangement of atoms in one molecule disposed relative to the atoms in the second molecule defined by the ORTEP view depicted in FIG. 4; or
(f) the two molecules in the asymmetric unit being conformationally oriented at an angle of about 65.2° relative to each other about the C1-N1 bond depicted in FIG. 5(a); or
(g) the two molecules being conformationally oriented at an angle of about 65.2° relative to each other about the C1-N1 bond defined by FIG. 5(b); or
(h) the comparative relative overlap of the second molecule vis-à-vis the conventional crystals depicted in FIG. 6.

It is intended that all the above descriptions of the relative spatial arrangement of the molecules in the propanil crystals of the present invention describe, individually and in specific combinations with each other, the crystalline propanil of the present invention. Accordingly, references to crystalline propanil of the present invention may be taken to denote references to crystalline propanil described in each of the above aspects or embodiments, either individually or in all contemplatable combinations thereof.

In another embodiment, the present invention relates to agrochemical compositions comprising the crystalline propanil.

In a preferred embodiment of the present invention, the agrochemical composition comprises from about 0.1% to about 100% by weight of the propanil crystalline modification.

According to another embodiment of the present invention, there is provided an agrochemical composition comprising the propanil crystalline modification along with other agronomically acceptable excipients.

In another embodiment of the present invention there are provided agrochemical combinations comprising the propanil crystalline modification along with one or more other pesticides.

Other active ingredients that can be combined with the propanil crystalline modification of the present invention are selected from pesticides such as herbicides, fungicides and insecticides.

In an embodiment, another active ingredient that can be combined with the propanil crystalline modification of the present invention is selected from but not limited to, a isoxazolidinone herbicide, a urea herbicide, a triazine herbicide, a hydroxybenzonitrile herbicide, a thiocarbamate herbicide, a pyridazine herbicide, chloroacetanilide herbicides; benzothiazole herbicides; carbanilate herbicides, cyclohexene oxime herbicides; picolinic acid herbicides; pyridine herbicides; quinolinecarboxylic acid herbicides; chlorotriazine herbicides, aryloxyphenoxypropionic herbicides, oxadiazolone herbicides; phenylurea herbicides, sulfonanilide herbicides; triazolopyrimidine herbicides, amide herbicides, pyridazine herbicides, dinitroaniline herbicides or combinations thereof.

In yet another embodiment of the present invention, another active ingredient that can be combined with the propanil crystalline modification of the present invention is selected from an amide herbicide such as allidochlor, amicarbazone, beflubutamid, benzadox, benzipram, bromobutide, cafenstrole, cyprazole, dimethenamid, dimethenamid-P, diphenamid, epronaz, etnipromid, fentrazamide, flucarbazone, flupoxam, fomesafen, halosafen, huangcaoling, isocarbamid, isoxaben, napropamide, napropamide-Mnaptalam, pethoxamid, propyzamide, quinonamid, saflufenacil, tebutam, tiafenacil, sulfonamide herbicide such as asulam, carbasulam, fenasulam, oryzalin, penoxsulam, pyroxsulam, aryloxycarboxylic acids such as MCPA-thioethyl, aryloxyphenoxypropionates such as clodinafop-propargyl, cyhalofop-butyl, diclofops, fluazifops, haloxyfops and its esters, haloxyfop-P and its esters, quizalofops, chloroacetamides such as acetolochlor, alachlor, butachlor, dimethenamid, metolachlor, propachlor, cyclohexanedione oximes such as alloxydim, butroxydim, clethodim, cloproxydim, cycloxydim, profoxydim, sethoxydim, tepraloxydim, tralkoxydim, benzamides such as isoxaben, benzoic acid derivatives such as dicamba, ethofumesate, dinitroanilines such as benfluralin, butralin, chlornidine, dinitramine, dipropalin, ethalfluralin, fluchloralin, isopropalin methalpropalin, nitralin, oryzalin, pendimethalin, prodiamine, profluralin, trifluralin, diphenyl ethers such acifluorfen, aclonifen, bifenox, chlomethoxyfen, chlornitrofen, etnipromid, fluorodifen, fluoroglycofen, fluoronitrofen, fomesafen, fucaomi, furyloxyfen, halosafen, lactofen, nitrofen, nitrofluorfen, oxyfluorfen, organophosphorus herbicides such as glufosinate and glyphosate, hydroxybenzonitriles such as bromoxynil, imidazolinones such as fenamidone, imazapic, imazamox, imazapic, imazapyr, imazethapyr, imazaquin, isoxazolidinones such as clomazone paraquat as bypyridylium, phenyl carbamates such as desmedipham, phenmedipham, phenylpyrazoles such as pyraflufen-ethyl, phenylpyrazolines such as pinoxaden, pyridinecarboxylic acids or synthetic auxins such as picloram, clopyralid, and triclopyr, pyrimidinyloxybenzoics such as bispyrtbac-sodium, sulfonylureas such as amidosulfuron, azimsulfuron, bensulfuron-methyl, chlorsulfuron, chlorimuron, cyclosulfamuron, ethoxysulfuron, flazasulfuron, flucetosulfuron, flupyrsulfuron, foramsulfuron, halosulfuron, imazosulfuron, mesosulfuron, metsulfuron-methyl, methiopyrisulfuron, monosulfuron, nicosulfuron, orthosulfamuron, oxasulfuron, primisulfuron, propyrisulfuron, pyrazosulfuron, rimsulfuron, sulfometuron, sulfosulfurontrifloxysulfuron, flazasulfuron, foramsulfuron, flupyrsulfuron-methyl-sodium, nicosulfuron, rimsulfuron, sulfosulfuron, tribenuron-methyl, trifloxysurlfuron-sodium, triflusulfuron, tritosulfuron, triazolopyrimidines such as penoxsulam, metosulam, florasulam, triketones such as mesotriones, sulcotrione, ureas such as diuron, linuron, phenoxycarboxylic acids such as 2,4-D, MCPA, MCPB, mecoprops and triazines such as atrazine, simazine and terbuthylazine.

In another embodiment, another active ingredient that can be combined with the propanil crystalline modification of the present invention is selected from but not limited to amide fungicides, acylamino acid fungicides, anilide fungicides, benzamide fungicides, sulfonamide fungicides, strobilurin fungicides, aromatic fungicides, benzimidazole fungicides, carbamate fungicides, carbanilate fungicides, conazole fungicides (imidazoles triazoles), copper fungicides, dithiocarbamate fungicides, imidazole fungicides, organophosphorus fungicides, oxazole fungicides, pyrazole fungicides, pyridine fungicides or combinations thereof.

According to another embodiment of the present invention another active ingredient that can be combined with the crystalline propanil of the present invention is selected from but not limited to arsenical insecticides, botanical insecticides, carbamate insecticides, benzofuranyl methylcarbamate insecticides, dimethylcarbamate insecticides, oxime carbamate insecticides, phenyl methylcarbamate insecticides, diamide insecticides, dinitrophenol insecticides, fluorine insecticides, formamidine insecticides, fumigant insecticides, inorganic insecticides, insect growth regulators, benzoylphenylurea chitin synthesis inhibitors, macrocyclic lactone insecticides, neonicotinoid insecticides, nereistoxin analogue insecticides, organochlorine insecticides, organophosphorus insecticides, organothiophosphate insecticides, heterocyclic organothiophosphate insecticides, phenyl organothiophosphate insecticides, phosphonate insecticides, phosphonothioate insecticides, phosphoramidate insecticides, phosphoramidothioate insecticides, phosphorodiamide insecticides, oxadiazine insecticides, oxadiazolone insecticides, phthalimide insecticides, physical insecticides, pyrazole insecticides, pyrethroid insecticides, pyrethroid ether insecticides, pyrimidinamine insecticides, pyrrole insecticides, quaternary ammonium insecticides, sulfoximine insecticides, tetramic acid insecticides, tetronic acid insecticides, thiazole insecticides, thiazolidine insecticides and thiourea insecticides.

According to an embodiment of the present invention, there is provided an agrochemical composition comprising the crystalline propanil along with other agronomically acceptable excipients.

In an embodiment of the present invention, the active ingredient that is added in combination with the propanil crystalline modification of the present invention is selected from a phenoxyacetic acid herbicides such as 2-(4-chloro-2-methylphenoxy)acetic acid or 2,4-D. Accordingly there is provided a composition comprising the crystalline modification of propanil, 2-(4-chloro-2-methylphenoxy)acetic acid and agronomically acceptable excipients. The composition comprises from about 20% to about 99% by weight of the propanil crystalline modification and from about 0.1% to about 40% by weight of phenoxyacetic acid herbicide.

In another embodiment of the present invention, the active ingredient that is added in combination with the crystalline modification of propanil of the present invention is selected from an isoxazolidinone herbicide such as clomazone. Accordingly there is provided a composition comprising crystalline modification of propanil, clomazone and agronomically acceptable excipients. The composition comprises from about 20% to about 99% by weight of the propanil crystalline modification and from about 0.1% to about 40% by weight of an isoxazolidinone herbicide.

According to another embodiment of the present invention, the active ingredient that is added in combination with the crystalline modification of propanil of the present invention is selected from pyridine herbicides such as triclopyr and its derivatives. Accordingly there is provided a composition comprising the crystalline modification of propanil, triclopyr and agronomically acceptable excipients. The composition comprises from about 20% to about 99% by weight of the propanil crystalline modification and from about 0.1% to about 40% by weight of a pyridine herbicides or its derivatives.

In another embodiment of the present invention, the active ingredient that is added in combination with the crystalline modification of propanil of the present invention is selected from sulfonyl urea herbicides such as halosulfuron, metsulfuronor bensulfuron or its derivatives. Accordingly there is provided a composition comprising the crystalline modification of propanil, halosulfuron, metsulfuron or bensulfuronor its derivatives and agronomically acceptable excipients. The composition comprises from about 20% to about 99% by weight of the propanil crystalline modification and from about 0.1% to about 40% by weight of a sulfonyl urea herbicide or its derivative.

In yet another embodiment of the present invention, the active ingredient that is added in combination with the crystalline modification of propanil of the present invention is selected from sulfonamide herbicides such as penoxsulam. Accordingly there is provided a composition comprising the crystalline modification of propanil, penoxsulam and agronomically acceptable excipients. The composition comprises from about 20% to about 99% by weight of the propanil crystalline modification and from about 0.1% to about 40% by weight of a sulfonamide herbicide or its derivative.

In an embodiment, the herbicide that can be combined with crystalline modification of propanil of the present invention is preferably selected from 2-(4-chloro-2-methylphenoxy)acetic acid, clomazone, 2,4-D, tricloypyr, halosulfuron, bensulfuron, metsulfuron-methyl, their derivatives and penoxsulam.

The compositions comprising crystal forms of the present invention includes both solid and liquid based formulations such as powders, granules, dry formulations, solutions, emulsions, suspensions and microencapsulations in polymeric substances. These formulations are produced in a known manner for example by mixing the crystal forms with auxiliaries suitable for the formulation of these active ingredients such as solvents/carriers, optionally with adjuvants such as surfactants, emulsifiers, dispersing agents, antifoaming agents, anti-freezing agents, colorants, wetting agents, anticaking agents, biocides, viscosity modifiers and binding agents. The composition content of these adjuvants is not particularly limiting and may be determined by a skilled technician in the art according to the conventional protocols.

In an embodiment of the present invention, the surfactants that can be additionally added to the compositions are selected from nonionic and/or anionic surfactants.

Examples of nonionic surfactants comprise alkylphenol alkoxylates, alcohol alkoxylates, fatty amine alkoxylates, polyoxyethylene glycerol fatty acid esters, castor oil alkoxylates, fatty acid alkoxylates, fatty amide alkoxylates, fatty polydiethanolamides, lanolin ethoxylates, fatty acid polyglycol esters, isotridecyl alcohol, fatty amides, methylcellulose, fatty acid esters, alkyl polyglycosides, glycerol fatty acid esters, polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers (polyethylene oxide/polypropylene oxide block copolymers) and mixtures thereof. Preferred nonionic surfactants are fatty alcohol ethoxylates, alkyl polyglycosides, glycerol fatty acid esters, castor oil alkoxylates, fatty acid alkoxylates, fatty amide alkoxylates, lanolin ethoxylates, fatty acid polyglycol esters and ethylene oxide/propylene oxide block copolymers and mixtures thereof Examples of anionic surfactants include alkylaryl sulfonates, phenyl sulfonates, alkyl sulfates, alkyl sulfonates, aryl alkyl sulfonates, alkyl ether sulfates, alkylaryl ether sulfates, alkyl polyglycol ether phosphates, polyaryl phenyl ether phosphates, alkyl sulfosuccinates, olefin sulfonates, paraffin sulfonates, petroleum sulfonates, taurides, sarcosides, salts of fatty acids, alkylnaphthalenesulfonic acids, naphthalenesulfonic acids and lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, alkyl phosphates, alkylaryl phosphates, for example tristyryl phosphates, and also polycarboxylates, such as, for example, polyacrylates, maleic anhydride/olefin copolymers, including the alkali metal, alkaline earth metal, ammonium and amine salts of the substances mentioned above and mixtures thereof. Preferred anionic surfactants are those which carry at least one sulfonate group, and in particular their alkali metal and their ammonium salts and mixtures thereof In an embodiment of the present invention, solvents suitable for use in the compositions of the present invention include water, aromatic solvents (for example Solvesso products, xylene, mix-xylene), alcohols (for example methanol, butanol, pentanol, benzyl alcohol), ketones (for example cyclohexanone, gamma-butyrolactone), pyrrolidones (NMP, NOP), ketonic solvents, glycols, acetates (glycol diacetate), carbonates such as propylene carbonates, fatty acid dimethylamides (for example N, N dimethyl octanamide, N, N dimethyl decanamide, Hallcomid, rhodiasolv adma10, fatty acids fatty acid esters and amino carboxylic acid esters (polarclean). In principle, solvent mixtures can also be used.

In an embodiment the compositions of the present invention comprises a crystallisation inhibitor which is usually employed for this purpose in agrochemical compositions.

In an embodiment of the present invention, the compositions comprise rheology modifier (or a viscosity modifying additive or a structuring agent). Suitable compounds are all those compounds usually employed for this purpose in agrochemical compositions. Examples include bentonites, attapulgites, polysaccharides, such as xanthan gum and kelzan gum.

In another embodiment of the present invention, the compositions comprise antifreeze agents. Suitable antifreeze agents are liquid polyols, for example ethylene glycol, propylene glycol or glycerol.

Common surface-active substances present in formulations of agrochemical active ingredients are suitable for use as emulsifiers. Examples are ethoxylated nonylphenols, polyethylene glycol ethers of linear alcohols, conversion products of alkylphenols with ethylene oxide and/or propylene oxide, ethylene oxide-propylene oxide block copolymers, polyethylene glycols and polypropylene glycols (Emulsogen PC), furthermore fatty acid esters, alkyl sulphonates, alkyl sulphates, aryl sulphates, ethoxylated arylalkylphenols, such as tristyryl-phenol-ethoxylate, furthermore ethoxylated and propoxylated arylalkylphenols as well as sulphated or phosphated arylalkylphenol-ethoxylates or -ethoxy- and -propoxylates.

In yet another embodiment of the present invention, the compositions comprise dispersing agents. All substances commonly used as dispersing agents in plant protection products are suitable for this purpose. Preferred dispersants are of anionic or nonionic nature and selected, for example, from polyethylene glycol/polypropylene glycol block copolymers, polyethylene glycol alkyl ethers, polypropylene glycol alkyl ethers, polyethylene glycol/polypropylene glycol ether block copolymers, alkylaryl phosphates, for example tristyryl phosphates, lignosulfonic acids, condensates of sulfonated naphthalenes with formaldehyde or with formaldehyde and phenol and, if appropriate, urea, and also condensates of phenolsulfonic acid, formaldehyde and urea, lignosulfite waste liquors and lignosulfonates, polycarboxylates, such as, for example, polyacrylates, maleic anhydride/olefin copolymers including the alkali metal, alkaline earth metal, ammonium and amine salts of the substances mentioned above.

In another embodiment of the present invention, the compositions comprise wetting agents. Preferred wetting agents are of anionic or nonionic nature and selected, for example, from naphthalenesulfonic acids including their alkali metal, alkaline earth metal, ammonium and amine salts, fatty alcohol ethoxylates, alkyl polyglycosides, glycerol fatty acid esters, castor oil alkoxylates, fatty acid alkoxylates, fatty amide alkoxylates, fatty polydiethanolamides, lanolin ethoxylates and fatty acid polyglycol esters.

In an embodiment of the present invention the compositions comprise a humectant selected from polyols like sucrose, glycerin or glycerol, triethylene glycol, tripropylene glycol, and propylene glycol.

In an embodiment there is provided a process for the preparation of compositions comprising crystalline propanil and agronomically acceptable excipients. The process for preparing such compositions is not particularly limiting.

Accordingly, in a preferred embodiment, there is provided a process for preparing compositions comprising crystalline propanil and agronomically acceptable excipients said process comprising:
  a) mixing crystalline modification of propanil with customary agronomically acceptable excipients;
  b) adding one or more other pesticides if required;
  c) grinding or pulverization if required; and
  d) granulating said mixture to obtain granular compositions.

In an embodiment of the present invention the process of adding the ingredients/and or other pesticides can be in any order.

In another embodiment of the present invention the step of granulating the mixture is not particularly limiting. Appropriate granulating processes are all conventional processes described in granulating technology for example spray drying, fluidized bed granulation, agglomeration, pan granulation and in particular extrusion granulation.

In another preferred embodiment there is provided a process for the preparation of compositions comprising crystalline propanil, said process comprising the steps of:
  a) preparing a slurry of crystalline propanil;
  b) adding other customary excipients;
  c) adding one or more other pesticides if required; and
  d) milling the slurry to desired particle size using suitable equipment.

In an embodiment of the present invention the step of preparing the slurry and the step of milling the slurry are not particularly limiting.

In another embodiment of the present invention the process of adding the ingredients can be in any order.

In another preferred embodiment there is provided a process for the preparation of compositions comprising crystalline propanil, said process comprising the steps of:
  a) preparing a solution of crystalline propanil in appropriate solvents;
  b) adding one or more other pesticides if required
  c) adding other customary excipients such as emulsifiers; and
  d) stirring the mixture as required.

In an embodiment of the present invention the step of preparing a solution of crystalline modification of propanil and the step of homogenizing the mixture are not particularly limiting.

In another embodiment of the present invention the process of adding the ingredients can be in any order.

The propanil crystalline modification of the present invention is suitable for combating weeds. Accordingly there is provided a method of combating weeds comprising contacting weeds or their locus with a herbicidally effective amount of crystalline modification of propanil.

The propanil crystalline modification of the present invention is suitable as the broad spectrum herbicide for controlling/killing different kind of broad leaf weeds, grasses and sedges.

Accordingly there is provided a method to control unwanted plants or to influence the growth of plants by treating said plants in the field with an effective amount of a herbicidal composition comprising crystalline modification of propanil.

In yet another embodiment of the present invention there is provided a method to control unwanted plants or to influence the growth of plants by treating said plants or their locus in the field with an effective amount of an herbicidal composition comprising a combination of crystalline propanil with one or more agrochemical active ingredients.

In another aspect, the present invention provides a method of controlling weeds by applying the crystalline propanil or a composition thereof.

In an embodiment, the method comprises administering the crystalline propanil along with one or more other pesticides.

In an embodiment, the one or more pesticide may be selected from:
(a) herbicides selected from a isoxazolidinone herbicide, a urea herbicide, a triazine herbicide, a hydroxybenzonitrile herbicide, a thiocarbamate herbicide, a pyridazine herbicide, chloroacetanilide herbicides; benzothiazole herbicides; carbanilate herbicides, cyclohexene oxime herbicides; picolinic acid herbicides; pyridine herbicides; quinolinecarboxylic acid herbicides; chlorotriazine herbicides, aryloxyphenoxypropionic herbicides, oxadiazolone herbicides; phenylurea herbicides, sulfonanilide herbicides; triazolopyrimidine herbicides, amide herbicides, pyridazine herbicides, dinitroaniline herbicides or combinations thereof;
(b) fungicides selected from amide fungicides, acylamino acid fungicides, anilide fungicides, benzamide fungicides, sulfonamide fungicides, strobilurin fungicides, aromatic fungicides, benzimidazole fungicides, carbamate fungicides, carbanilate fungicides, conazole fungicides (imidazoles triazoles), copper fungicides, dithiocarbamate fungicides, imidazole fungicides, organophosphorus fungicides, oxazole fungicides, pyrazole fungicides, pyridine fungicides or combinations thereof; and
(c) insecticides selected from arsenical insecticides, botanical insecticides, carbamate insecticides, benzofuranyl methylcarbamate insecticides, dimethylcarbamate insecticides, insecticides, dinitrophenol insecticides, fluorine insecticides, formamidine insecticides, fumigant insecticides, inorganic insecticides, insect growth regulators, benzoylphenylurea chitin synthesis inhibitors, macrocyclic lactone insecticides, neonicotinoid insecticides, nereistoxin analogue insecticides, organochlorine insecticides, organophosphorus insecticides, organothiophosphate insecticides, heterocyclic organothiophosphate insecticides, phenyl organothiophosphate insecticides, phosphonate insecticides, phosphonothioate insecticides, phosphoramidate insecticides, phosphoramidothioate insecticides, phosphorodiamide insecticides, oxadiazine insecticides, oxadiazolone insecticides, phthalimide insecticides, physical insecticides, pyrazole insecticides, pyrethroid insecticides, pyrethroid ether insecticides, pyrimidinamine insecticides, pyrrole insecticides, quaternary ammonium insecticides, sulfoximine insecticides, tetramic acid insecticides, tetronic acid insecticides, thiazole insecticides, thiazolidine insecticides and thiourea insecticides.

The composition according to the present invention can also be prepared by tank-mixing the active ingredient with auxiliaries suitable for the formulation of these active ingredients or alternatively may be sold as a kit of parts containing actives and other ingredients that may be mixed prior to spraying.

Accordingly, in an embodiment, the present invention provides a multi-pack agrochemical product comprising:
a) a first container containing crystalline modification of propanil
b) a second container containing other agrochemical adjuvants/surfactants/solvents and
c) an instruction manual instructing the user to admix said ingredients before application Accordingly, in another embodiment, the present invention provides a multi-pack agrochemical product comprising:
a) a first container containing crystalline modification of propanil
b) a second container containing other agrochemical adjuvants/surfactants/solvents
c) optionally a third container containing one or more other pesticides; and
d) an instruction manual instructing the user to admix said ingredients before application.

The methods of application of pesticidal compositions as well as the pesticidal mixtures according to the present invention are not particularly limiting. It can be simultaneous application of either a pre-mix or tank mix of active ingredients with auxiliaries suitable for the formulation or it can be a sequential application of one after the other.

The invention shall now be described with reference to the following specific examples. It should be noted that the examples appended below illustrate rather than limit the invention and that those skilled in the art will be able to design many alternative embodiments without departing from the scope of the present invention.

Preparation of Propanil crystals using methanol as solvent (Prior art 1 or PA1) as per GB903766 has been reproduced here for comparison with the propanil crystalline modification of the present invention.

Example 1: Preparation of the Crystalline Modification of Propanil of the Present Invention by Crystallisation from Dichloromethane Technical propanil was procured from market.
497.7 ml of dichloromethane was charged into a glass kettle and 700 gm of technical propanil was added while stirring at 25° C. The slurry was stirred and heated to 38-40° C. until propanil was completely dissolved to obtain a clear solution. The solution was cooled slowly to about 28-30° C. while stirring. The mass was further cooled to about 5-10° C. while stirring. The mass was stirred at 5-10° C. for a period of 1 hour and filtered at 5-10° C. The crystals were dried under vacuum at 20-25° C. to obtain 579 gm (82.7% yield, 99.7% by GC)) of product.

Example 2: Preparation of the Crystalline Modification of Propanil According to the Present Invention by Crystallisation from a Mixture of Dichloromethane and Hexane 100 ml of dichloromethane was charged in a glass kettle and 100 gm of technical propanil was added while stirring at 25° C. The mass was heated to 50° C. while stirring and 200 ml of n-hexane was added slowly. The solution was stirred at 50° C. for an hour and allowed to cool slowly to 10-15° C. and maintained at the same temperature for an hour. The crystals were filtered at 10-15° C. The crystals were dried under vacuum to obtain 95 gm of product.

Example 3: Large Scale Preparation of the Crystalline Modification of Propanil of the Present Invention by Crystallisation from Dichloromethane 4679 grams of dichloromethane was charged in a glass kettle. 5000 grams of propanil were added followed by stirring and heating the mass to about 45° C. so that the propanil dissolved completely in the solvent giving a pale yellow to pale brown colored solution. The reaction mass was cooled under stirring to about 30° C. in about 3-4 hours. The slurry was further cooled under stirring to about 10° C. and maintained at that temperature for about 1 hour. The slurry was filtered and washed using chilled dichloromethane at about 10° C. The crystals were dried under vacuum at about 55-60° C. to get 3945 grams (79%) of the crystalline product.

Example 4: A Dry Formulation Comprising the Crystalline Modification of Propanil was Prepared According to the Present Invention as Follows

| Ingredients | Quantity (% w/w) |
| --- | --- |
| crystalline propanil | 62.5 |
| sodium alkylnaphthalenesulfonate, formaldehyde condensate | 7.36 |
| docusate sodium | 0.96 |
| sodium lignosulfonate | 4.09 |
| precipitated silica | 1.58 |
| kaolin (QS) | 23.51 |

The composition was prepared by the following manner:

Required quantity of crystalline modification of propanil was mixed with required quantity of sodium alkylnaphthalenesulfonate formaldehyde condensate, docusate sodium, sodium lignosulfonate, precipitated silica and kaolin. Sufficient quantity of water was added to make dough of the composition. Further the dough was granulated using extrusion granulating process to prepare granules. The granules were then dried.

Example 5: A Dry Formulation Comprising the Crystalline Modification of Propanil was Prepared According to the Present Invention as Follows

| Ingredients | Quantity (% w/w) |
| --- | --- |
| crystalline propanil | 82.00 |
| blend of anionic and nonionic surfactants | 7.5 |
| sodium lignosulfonate | 4.0 |
| precipitated Silica | 1.2 |
| antifoam | 0.5 |
| alkyl naphthalene sulfonate | 4.0 |
| kaolin (QS) | 1.5 |

Example 6: A Granular Formulation Comprising the Crystalline Modification of Propanil and 4-Chloro-2-Methylphenyl Acetic Acid was Prepared According to the Present Invention as Follows

| Ingredients | Quantity (% w/w) |
| --- | --- |
| crystalline propanil | 60.00 |
| potassium polycarboxylate | 7.36 |
| sodium alkyl sulfate | 3.50 |
| modified sodiumlignosulfonate | 4.00 |
| precipitated silica | 1.58 |
| 4-chloro-2-methylphenyl acetic acid | 7.5 |
| kaolin (QS) | 16.06 |

Example 7: A Granular Formulation Comprising the Crystalline Modification of Propanil and Bensulfuron Methyl was Prepared According to the Present Invention as Follows

| Ingredients | Quantity (% w/w) |
| --- | --- |
| crystalline propanil | 62.5 |
| sodium alkylnaphthalenesulfonate, formaldehyde condensate | 7.36 |
| docusate sodium | 0.96 |
| sodium lignosulfonate | 4.09 |
| precipitated silica | 1.58 |
| bensulfuron methyl | 0.5 |
| kaolin (QS) | 23.01 |

Example 8: A Granular Formulation Comprising the Crystalline Modification of Propanil and Metsulfuron-Methyl was Prepared According to the Present Invention as Follows

| Ingredients | Quantity (% w/w) |
| --- | --- |
| crystalline propanil | 62.5 |
| sodium alkylnaphthalenesulfonate, formaldehyde condensate | 7.36 |
| docusate sodium | 0.96 |
| sodium lignosulfonate | 4.09 |
| precipitated silica | 1.58 |
| metsulfuron-methyl | 0.5 |
| kaolin (QS) | 23.01 |

Example 9: a Granular Formulation Comprising the Crystalline Modification of Propanil and Halosulfuron Methyl was Prepared According to the Present Invention as Follows

| Ingredients | Quantity (% w/w) |
| --- | --- |
| crystalline propanil | 62.5 |
| sodium alkylnaphthalenesulfonate, formaldehyde condensate | 7.36 |

-continued

| Ingredients | Quantity (% w/w) |
|---|---|
| docusate sodium | 0.96 |
| sodium lignosulfonate | 4.09 |
| precipitated silica | 1.58 |
| halosulfuron methyl | 0.5 |
| kaolin (QS) | 23.01 |

Example 10: Suspension Concentrate Comprising the Crystalline Modification of Propanil and Bensulfurone Methyl was Prepared According to the Present Invention as Follows

| Ingredients | Quantity(% w/w) |
|---|---|
| crystalline propanil | 41.52 |
| bensulfuron methyl | 0.33 |
| sulfated derivative of alky aryl phenol ethoxylate | 3.00 |
| EOPO copolymer | 1.75 |
| alkyl naphthalene sulfonate formaldehyde copolymer | 3.00 |
| biocide | 0.01 |
| glycol | 7.00 |
| silica | 0.50 |
| antifoam | 0.50 |
| structuring agent | 12.00 |
| water | QS |

The composition was prepared by the following manner:

The required quantity of water was charged into the slurry preparation vessel. Required quantity of sulfated derivative of alky aryl phenol ethoxylate, EOPO copolymer and alkyl naphthalene sulfonate formaldehyde copolymer was added to the vessel while stirring followed by other excipients. Stirring continued until the solution is homogenized. Required quantity of propanil and benzulfuron methyl was added to the solution to form uniform slurry followed by milling to get the desired particle size.

Example 11: Suspension Concentrate of Crystalline Modification of Propanil was Prepared as Follows

| Ingredients | Quantity (% w/w) |
|---|---|
| crystalline propanil | 41.61 |
| sulfated derivative of alky aryl phenol ethoxylate | 2.50 |
| EOPO copolymer | 1.50 |
| alkyl naphthalene sulfonate formaldehyde copolymer | 2.50 |
| biocide | 0.08 |
| glycol | 8.00 |
| silica | 0.50 |
| antifoam | 0.50 |
| structuring agent | 0.21 |
| water | QS |

Example 12: Emulsifiable Concentrate of Crystalline Modification of Propanil and Clomazone was Prepared as Follows

| Ingredient | Quantity % w/w |
|---|---|
| crystalline propanil | 42.00 |
| clomazone | 10.63 |
| emulsogen PC | 10.125 |
| atlox 3418 | 04.575 |
| rhodiasolv adma 10 | 20.00 |
| mix-xylene (QS) | 12.67 |

The composition was prepared by the following manner:

Required quantity of solvents mix-xylene and rhodiasolv adma 10 was charged into the vessel followed by the addition of required quantity of propanil while stirring.

Stirring was continued until propanil dissolved completely. It was followed by the addition of required quantity of clomazone while stirring to get a homogenized solution. Required quantity of emulsogen PC and atlox 3418 were added and stirred to get an emulsifiable concentrate.

Example 13: Emulsifiable Concentrate of Crystalline Modification of Propanil and Triclopyr Butyl Ester was Prepared as Follows

| Ingredients | Quantity (% w/w) |
|---|---|
| crystalline propanil | 35.91 |
| triclopyr butyl ester | 5.42 |
| EOPO copolymer | 1.01 |
| aryl amine sulfonate | 15.00 |
| aromatic hydrocarbonsolvent | QS |

Field Trials:

Protocol: Field trials were carried out using the compositions of the crystalline modification of propanil prepared according to the present invention as the broad spectrum herbicide. The composition were optionally mixed with other tank mix auxiliaries and applied at an application rate of 1-2 kg/ha to crop and non-crop land containing many broad leaf weeds, grasses and sedges. Dose of commercial conventional formulation of propanil (Spada 60) is 4.0 kg/ha. Observations of 7 to 22 days after treatment have been summarized in below tables demonstrating the bio-efficacy of the compositions.

Field Trial 1: Weed Control Study in Paddy Field Using Formulations Comprising the Crystalline Modification of Propanil A formulation comprising crystalline modification of Propanil, (Example 4) a formulation comprising propanil recrystallised from aqueous methanol as per the literature (prior art 1 or PA1) as well as market sample of Propanil (Propanil 60 DF, Spada 60) for the same dosage as well for a higher dosage of 4.0 kg/ha were tested for weed control in paddy field. The weeds include *Ischaemun rugosum, Leptochloa filiformie, Echinochloa colonum, Jussiaea linifolia* and *Cyperus ferax*.

TABLE 4

% weed control 15 days after application

| Product | Rate kg/ha | Grass | Echinochloa colonum | Ischaemun rugosum | Leptochloa sp. | Broad spectrum | Jussiaea linifolia | Cyperus ferax |
|---|---|---|---|---|---|---|---|---|
| Ex. 4 | 2 | 95 | 90 | 95 | 95 | 95 | 90 | 95 |
| Spada 60 | 2 | 75 | 75 | 80 | 75 | 80 | 80 | 85 |
| PA1 | 2 | 80 | 70 | 80 | 90 | 85 | 85 | 90 |
| Spada 60 | 4 | 95 | 95 | 95 | 95 | 80 | 80 | 95 |

TABLE 5

% weed control 22 days after application

| Product | Rate kg/ha | Grass | Echinochloa colonum | Ischaemun rugosum | Leptochloa sp. | Broad spectrum | Jussiaea linifolia | Cyperus ferax |
|---|---|---|---|---|---|---|---|---|
| Ex. 4 | 2 | 95 | 95 | 95 | 95 | 95 | 95 | 95 |
| Spada 60 | 2 | 85 | 85 | 85 | 85 | 85 | 90 | 85 |
| PA1 | 2 | 90 | 90 | 90 | 90 | 85 | 85 | 90 |
| Spada 60 | 4 | 98 | 98 | 98 | 90 | 90 | 98 | 100 |

From the above results it has been observed that formulations comprising the crystalline propanil prepared according to Example 4 showed good weed control at lower application rate of 2 kg/ha. It has been noted that at any given rate of application, formulations comprising the crystalline modification of propanil showed higher bio-efficacy and higher consistency compared to Spada 60 (Propanil 60 DF, commercial sample). More particularly, it has been observed that formulations comprising the crystalline modification of propanil exhibited better bio-efficacy at a much lower application rate of 2.0 kg/ha than Spada 60 at an application rate of 4.0 kg/ha which in turn resulted in an effective use of the herbicide at a lower dosage. Thus it was concluded that formulations comprising the crystalline propanil can be effectively employed as a broad spectrum herbicide at a lower dosage with better bio-efficacy compared to other conventional propanil based formulations. It was also observed that formulations comprising the crystalline propanil according to the present invention demonstrated the best weed control across all weeds and appeared to be twice as biologically active than the conventional market sample.

Field Trial 2: Weed Control Study in Paddy Field Using a Combination of the Crystalline Modification of Propanil and Bensulfuron Methyl.

A combination of crystallinepropanil and bensulfurone methyl (Example 10) was tested against a conventional mixture of propanil and bensulfurone methyl (Propadax) for weed control in paddy field containing many broad leaf weeds, grasses and sedges. The mixture is tested at different dosages to study the efficacy of the mixtures. The weeds in the field included Echinochloa colona, Eleusine indica, Paspalum boscianum, Senna obstusifolia, Eclipta alba, Ipomoea triloba, Cyperus rotundus and Cyperus iria. Observations of 5 to 7 days after treatment have been summarized in below tables demonstrating the bio-efficacy of the combinations according to the present invention.

TABLE 6

% weed control 5 days after application

| treatments | grasses | broadleaves | sedges |
|---|---|---|---|
| Example 10 (25%) | 98 | 99 | 86.5 |
| Propadax (25%) | 92.5 | 91.5 | 60 |

TABLE 7

% weed control 7 days after application

| treatments | grasses | broadleaves | sedges |
|---|---|---|---|
| Example 10 (50%) | 90.5 | 89.5 | 91 |
| Propadax (50%) | 84 | 74.5 | 73 |
| Example 10 (25%) | 92 | 98 | 72.5 |
| Propadax (25%) | 87.5 | 82.5 | 40 |

It has been observed that the combination according to the present invention comprising crystalline propanil and bensulfuron methyl provided a better control on the weeds compared to the conventional mixture. It has been noted that at a lower dosage of about 50% and about 25%, the combination according to the present invention led to an acceptable weed control compared to the conventional mixtures. The mixture according to the present invention is found to be more bio efficacious for different kind of weeds from grasses, broadleaves and sedges. Thus it has been further confirmed that the crystalline modification of the present invention exhibits better bio efficacy and is useful in lower dosages compared to the conventional propanil based compositions.

The invention claimed is:

1. A crystalline propanil characterized by at least one of the following properties:
    (a) the 2θ and d-spacings parameters described in below table

| d(A°) | 2θ |
|---|---|
| 7.064 ± 0.1° | 12.51 ± 0.2° |
| 5.92 ± 0.1° | 14.93 ± 0.2° |
| 5.168 ± 0.1° | 17.11 ± 0.2° |
| 4.464 ± 0.1° | 19.87 ± 0.2° |
| 4.155 ± 0.1° | 21.35 ± 0.2° |
| 4.065 ± 0.1° | 21.83 ± 0.2° |
| 3.875 ± 0.1° | 22.91 ± 0.2° |
| 3.771 ± 0.1° | 23.55 ± 0.2° |
| 3.57 ± 0.1° | 24.91 ± 0.2° |
| 3.41 ± 0.1° | 26.09 ± 0.2° |
| 3.047 ± 0.1° | 29.27 ± 0.2° |
| 2.782 ± 0.1° | 32.13 ± 0.2° |
| 2.8742 ± 0.1° | 31.07 ± 0.2° |
| 2.363 ± 0.1° | 38.13 ± 0.2° |
| 2.258 ± 0.1° | 39.91 ± 0.2°; | or
(b) the structural coordinates described in below table;

| Parameter | Value |
|---|---|
| Crystal system | Monoclinic |
| Space group | $P2_1/c$ |
| a | 17.8853(2) Å |
| b | 11.6179(1) Å |
| c | 9.8524(9) Å |
| α | 90.00° |
| β | 92.761(6)° |
| γ | 90.00° |
| Volume | 2044.8(3) Å$^3$ |
| Z | 4 |
| Density (calculated) | 1.417 g/cc. |

2. The crystalline propanil according to claim 1, wherein said crystalline propanil exhibits an X-ray diffraction pattern having characteristic peaks expressed in 2θ (±0.2°) at least three of the following positions: 12.51, 14.93, 17.11, 19.8, 21.35, 21.83, 22.91, 23.55, 24.91, 26.09, 29.27, 32.13, 31.07, 38.13 and 39.91.

3. The crystalline propanil according to claim 1, wherein said crystalline propanil exhibits an X-ray diffraction pattern having characteristic peaks expressed in 2θ (±0.2°) at 12.51, 14.93, 17.11, 19.8, 21.35, 21.83, 22.91, 23.55, 24.91, 26.09, 29.27, 32.13, 31.07, 38.13 and 39.91.

4. The crystalline propanil according to claim 1, comprising crystals of propanil having two molecules in its asymmetric unit, said molecules being oriented in opposite directions.

5. The crystalline propanil according to claim 1, comprising crystals of propanil having two molecules in its asymmetric unit, said two molecules being conformationally oriented at an angle of about 65.2° relative to each other about the C1-N1 bond.

6. The crystalline propanil according to claim 1, crystallized from a halogenated hydrocarbon solvent.

7. The crystalline propanil according to claim 6, wherein said halogenated hydrocarbon solvent is selected from halogenated lower hydrocarbons from C1 up to C6 carbon atoms.

8. The crystalline propanil according to claim 6, wherein said halogenated hydrocarbon solvent is selected from the group consisting of dichloromethane, dichloropropane, trichloroethane, chloroform and dichloroethane.

9. The crystalline propanil according to claim 1, crystallized from a mixture of halogenated hydrocarbon solvent and one or more organic solvents.

10. The crystalline propanil according to claim 9, wherein said organic solvent is a non-polar organic solvent.

11. The crystalline propanil according to claim 10, wherein said non-polar organic solvent is selected from aliphatic or aromatic hydrocarbon solvents or ether solvents.

12. The crystalline propanil according to claim 11, wherein said non-polar organic solvent is selected from pentane, cyclopentane, hexane, cyclohexane, heptane, octane, benzene, toluene, 1,4-dioxane, or diethyl ether.

* * * * *